United States Patent [19]

Fujino et al.

[11] Patent Number: 4,845,245

[45] Date of Patent: Jul. 4, 1989

[54] PROCESS FOR PRODUCING 3,3-BIS-(4-DIMETHYLAMINOPHENYL)-6-DIMETHYLAMINOPHTHALIDE

[75] Inventors: Yoshiharu Fujino; Hajime Kawai, both of Tsuzuki; Katsuhiko Tsunemitsu, Kyoto, all of Japan

[73] Assignee: Yamada Chemical Co., Ltd., Kyoto, Japan

[21] Appl. No.: 76,624

[22] Filed: Jul. 23, 1987

[30] Foreign Application Priority Data

May 18, 1987 [JP] Japan .................. 62-120934

[51] Int. Cl.[4] .................. C07D 307/88; C07C 101/54
[52] U.S. Cl. .................. 549/304; 562/441
[58] Field of Search .................. 549/304; 562/441

[56] References Cited

U.S. PATENT DOCUMENTS

| 4,076,728 | 2/1978 | Maulding | 260/343.4 |
| 4,233,223 | 11/1980 | Seibert | 260/343.4 |

FOREIGN PATENT DOCUMENTS

| 0008118 | 1/1981 | European Pat. Off. |
| 0082394 | 6/1983 | European Pat. Off. |
| 1325029 | 8/1973 | United Kingdom |
| 1341040 | 12/1973 | United Kingdom |
| 1347467 | 2/1974 | United Kingdom |
| 1359899 | 7/1974 | United Kingdom |
| 1395627 | 5/1975 | United Kingdom |
| 1416484 | 12/1975 | United Kingdom |
| 1563598 | 12/1975 | United Kingdom |
| 1548672 | 7/1979 | United Kingdom |
| 2042577B | 9/1980 | United Kingdom |
| 2102444B | 2/1983 | United Kingdom |

*Primary Examiner*—Joseph P. Brust
*Attorney, Agent, or Firm*—Nixon & Vanderhye

[57] ABSTRACT

Disclosed herein is a process for producing 3,3-bis-(4-dimethylaminophenyl)-6-dimethylaminophthalide, which process comprises oxidizing 2-[4,4'-bis-(dimethylamino)-benzhydryl]-5-dimethylaminobenzoic acid in an aqueous solution of a mineral acid of pH of from 2.0 to 4.0 with air, oxygen or a gas containing oxygen in the presence of at least one catalyst selected from the group consisting of compounds of iron, copper, cobalt, nickel, chromium, vanadium and manganese.

3 Claims, No Drawings

PROCESS FOR PRODUCING 3,3-BIS-(4-DIMETHYLAMINOPHENYL)-6-DIMETHYLAMINOPHTHALIDE

BACKGROUND OF THE INVENTION

The present invention relates to a process for producing 3,3-bis-(4-dimethylaminophenyl)-6-dimethylaminophthalide(crystalviolet lactone, hereinafter referred to as CVL), and more in detail, the present invention relates to (1) a process for producing CVL, which process comprises oxidizing 2-[4,4'-bis-(dimethylamino)-benzhydryl]-5-dimethylaminobenzoic acid in an aqueous mineral acid solution of pH of from 2.0 to 4.0 in the presence of at least one kind of catalyst selected from the group consisting of compounds of iron, copper, cobalt, nickel, chromium, vanadium and manganese by using air, oxygen or a gas containing oxygen, and (2) a process for producing CVL, which process comprises slowly adding tetramethyl-4,4'-diaminobenzhydrol into an aqueous mineral acid solution of pH of from 1.5 to 3.0 containing m-dimethyl-aminobenzoic acid, thereby forming 2-[4,4'-bis-(dimethylamino)-benzhydryl]-5-dimethylaminobenzoic acid, adding a catalyst comprising a compound of transition metal to the reaction mixture and oxidizing the thus formed 2-[4,4'-bis-(dimethylamino)-benzhydryl]-5-dimethylaminobenzoic acid in the resultant reaction mixture by using air, oxygen or a gas containing oxygen.

Although CVL itself is colourless or nearly colourless, it has a property of rapidly developing blue-violet colour in the case of bringing CVL into close contact with an electron-accepting substance, for instance, an organic acid, acid clay, phenol-formalin resin, a metal salt of an aromatic carboxylic acid and bisphenol A, and CVL is most broadly used as the pigment for recording materials such as pressure-sensitive recording paper sheets, heat-sensitive recording paper sheets, etc.

As the process for producing CVL, although many processes wherein 2-[4,4'-bis-(dimethylamino)-benzhydryl]-5-dimethylaminobenzoic acid(hereinafter referred to as LC) is oxidized into CVL have been known, it is difficult to obtain CVL of a high quality in a high yield because of the complexity of the steps of production and the large amount of the by-products due to decomposition.

For instance, in the process of oxidizing LC in an aqueous mineral acid solution with lead peroxide or potassium permanganate (refer to U.S. Pat. No. 2,417,897), in the process of oxidizing LC in an organic solvent such as glacial acetic acid, chloroform, etc. with oxygen in the presence of a metal complex [refer to Japanese Patent Application Laid-Open (KOKAI) No. 48-25730 (1973) (U.S. Pat. No. 3,828,071)] and also in the process of oxidizing LC in a liquid mixture of a nonaqueous solvent of hydrocarbon series and water with hydrogen peroxide in the presence of an acid catalyst [refer to Japanese Patent Application Laid-Open (KOKAI) No. 52-78867 (1977)], a large amount of tarry by-products is formed, thereby remarkably reducing the yield and the quality of CVL, and such a process requires the complex step such as the recovery of the organic solvent. Furthermore, in the process of oxidizing LC with hydrogen peroxide in an aqueous solution or a water soluble organic solvent in the presence of an alkali [refer to Japanese Patent Application Laid-Open (KOKAI) No. 52-31384 (1977)] and also in the process of oxidizing LC with hydrogen peroxide, oxygen, or air in an aqueous alkaline solution in the presence of a catalyst comprising a compound of cobalt or copper [refer to Japanese Patent Publication No. 59-19548 (1984) (U.S. Pat. No. 4,271,075)], a large amount of the unreacted substance is contained in the reaction product, thereby forming lumpy materials. Namely, the reaction hardly proceeds and the yield and the quality of CVL are very poor.

Besides, as the process for synthesizing LC as the intermediate for producing CVL, a process of reacting m-dimethylaminobenzoic acid(hereinafter referred to as DABA) with tetramethyl-4,4'-diaminobenzhydrol(hereinafter referred to as MH) in an aqueous solution of sulfuric acid (refer to U.S. Pat. No. 3,842,103) and a process of the reaction by dropping an aqueous sulfuric acid solution of MH into an aqueous sulfuric acid solution of DABA(refer to German Patent No. 2156648) have been known, however, in each of the two processes, the amount of the by-products due to decomposition is large and the yield and the quality of LC are extremely low.

It has been known that the yield and the quality of CVL synthesized by oxidation of LC are generally influenced by the quality of LC and accordingly, the isolation and purification of LC are carried out ordinarily before subjecting LC to oxidation. For instance, although there is a method of treating LC of a mixture with an aromatic hydrocarbon or a water-insoluble alkane [refer to Japanese Patent Application Laid-Open (KOKAI) No. 53-115740 (1978)(Canadian Patent 1087202)], there are the defects that the recovery of the solvent is troublesome and the loss of LC is large in the treatment of recovery thereof.

Moreover, the process for producing CVL consists essentially of the first step of reacting DABA with MH to form LC and the second step of producing CVL by oxidizing the thus obtained LC. According to the conventional process, LC obtained in the first step is generally separated and purified and then the separated and purified LC is used as the starting material in the second step. However, since the loss of LC accompanying the isolation and purification thereof is large, a method is also considered wherein the reaction mixture obtained in the first step is used as the starting material in the second step without separating and purifying, and the reaction of the second step is continuously carried out with the first step.

However, in such a method of continuously carrying out the reaction of the first step and the reaction of the second step, not only the remaining raw material, the decomposition products of the raw material, the by-products of reaction, etc. of the first step badly influence the yield of CVL in the second step but also, according to the conditions in the second step, the operations such as the separation of the tarry by-products and the recovery of the solvent accompanying the purification of the final objective material (CVL) uselessly complexed.

Particularly, in the technique of the first step, a large amount of by-products other than LC is formed, and in consideration of only the above-mentioned point, the process of continuously carrying out the reaction of the first step and the reaction of the second step has been inadequate.

As a result of the present inventors' earnest studies for solving the defects of the conventional process for synthesizing CVL, it has been found by the present inventors that (1) LC of an extremely high quality can be obtained in a high yield by adding MH into an aqueous mineral acid solution of pH of from 1.5 to 3.0 containing DABA, and CVL of a high quality can be obtained in a high yield in a short time by oxidizing LC as the intermediate of the production of CVL, in an aqueous mineral acid solution of pH of from 2.0 to 4.0 in the presence of a catalyst comprising a compound of a transition metal selected from the group consisting of iron, copper, cobalt, nickel, chromium, vanadium and manganese by using air, oxygen or a gas containing oxygen or (2) CVL can be obtained in a continuous process from DABA and MH by slowly adding MH into an aqueous mineral acid solution of pH of from 1.5 to 3.0 containing DABA, thereby forming LC, then adding the catalyst comprising the compound of the transition metal to the reaction mixture and oxidizing the thus formed LC in the resultant reaction mixture with air, oxygen or a gas containing oxygen, and on the basis of the

SUMMARY OF THE INVENTION

In a first aspect of the present invention, there is provided a process for producing 3,3-bis-(4-dimethylamino-phenyl)-6-dimethylaminophthalide, which process comprises oxidizing 2-[4,4'-bis-(dimethylamino)-benzhydryl]-5-dimethylaminobenzoic acid in an aqueous mineral acid solution of pH of from 2.0 to 4.0 in the presence of at least one catalyst selected from the group consisting of compounds of iron, copper, cobalt, nickel, chromium, vanadium and manganese by using air, oxygen or a gas containing oxygen.

In a second aspect of the present invention, there is provided a process for producing 2-[4,4'-bis-(dimethylamino)-benzhydryl]-5-dimethylaminobenzoic acid as an intermediate of CVL, which process comprises slowly adding tetramethyl-4,4'-diaminobenzhydrol into an aqueous mineral acid solution of pH of from 1.5 to 3.0 containing m-dimethylaminobenzoic acid.

In a third aspect of the present invention, there is provided a process for producing 3,3-bis-(4-dimethylaminophenyl)-6-dimethylaminophthalide, which process comprises slowly adding tetramethyl-4,4'-diaminobenzhydrol into an aqueous mineral acid solution of pH of from 1.5 to 3.0 containing m-dimethylaminobenzoic acid, thereby forming 2-[4,4'-bis-(dimethylamino)-benzhydryl]-5-dimethylaminobenzoic acid, then adding a catalyst comprising a compound of a transition metal to the reaction mixture and oxidizing the thus formed 2-[4,4'-bis-(dimethylamino)-benzhydryl]-5-dimethylaminobenzoic acid in the resultant reaction mixture by using air, oxygen or a gas containing oxygen.

DETAILED DESCRIPTION OF THE INVENTION

As the mineral acid used in the reaction of DABA and MH, hydrochloric acid and sulfuric acid may be mentioned. As the mean particle diameter of DABA, that of not larger than 30 μm, preferably not larger than 5 μm, is preferred. As the mean particle diameter of MH, that of not larger than 50 μm, preferably not larger than 10 μm, is preferred.

The reaction of DABA and MH is preferably carried out at a temperature of from 50 to 100° C., preferably from 60° to 80° C., and it is advantageous to add MH as slowly as possible. Further, the addition of a surfactant, for instance, polyoxyethylene alkyl ether to the reaction system is effective for uniformly dispersing the reaction mixture.

The reaction of DABA and MH proceeds under the most suitable reaction conditions at pH of from 1.5 to 3.0, preferably from 2.0 to 3.0 of the aqueous solution of a mineral acid, preferably sulfuric acid, and the reaction is remarkably accelerated under these conditions and only a small amount of by-products is formed.

LC formed at the above-mentioned pH range does not dissolve so much in the reaction solution, and on the other hand, DABA and MH dissolve well in the reaction solution. Accordingly, MH added thereto rapidly dissolves in the reaction solution and reacts with DABA. Furthermore, DABA suspending in the reaction solution dissolves rapidly with the separation of LC which is formed by the reaction and accordingly, the pH of the reaction solution is kept within the above-mentioned range. As a result, LC is formed smoothly and the objective product is obtained in a high yield. Furthermore, since the impurities in DABA and MH and the by-products formed by decomposition dissolve well in the reaction solution at the above-mentioned pH range, such impurities and by-products can be completely removed only by filtering the thus separated LC after reaction and washing the thus filtered LC with water, and LC of a high quality can be obtained.

As the concrete example of the transition metal compound such as compounds of iron, copper, cobalt, nickel, chromium, vanadium and manganese, used as the catalyst in the oxidation of LC, ferric chloride, ferrous sulfate, cupric chloride, copper sulfate, copper acetate, cobalt chloride, cobalt sulfate, cobalt acetate, manganese chloride, manganese sulfate, chromium sulfate, nickel sulfate and vanadium sulfate may be mentioned. As the mineral acid used in the oxidation reaction, hydrochloric acid and sulfuric acid may be mentioned.

It is preferable that LC used in the present invention is in a state as minute as possible, preferably in a state of minute particles of a mean particle diameter of not larger than 20 m, more preferably not larger than 10 μm.

The oxidation of LC is advantageously carried at a temperature of from 40° to 120° C., preferably from 80° to 100° C., and it is preferable to introduce air, oxygen or a gas containing oxygen as minute bubbles into the reaction mixture. The pressure of the reaction vessel in the oxidation is not limited, and the oxidation can be conducted under pressure, normal pressure or reduced pressure.

Furthermore, in order to uniformly disperse the reaction mixture, the addition of a surfactant, for instance, polyoxyethylene alkyl ether, to the reaction system is preferable.

The aqueous mineral acid solution, preferably the aqueous solution of sulfuric acid used in the oxidation of LC scarcely dissolves CVL at pH of from 2.0 to 4.0, preferably from 2.0 to 3.0, and on the other hand, dissolves LC and the impurities contained in LC or the by-products of reaction very well. As a result, CVL formed by oxidation separates out from the reaction solution immediately, and the formation of CVL is smoothly carried out to obtain a high yield of CVL.

Furthermore, in the transition metal compound as the catalyst of the present invention, the compounds of copper and cobalt is preferable since these metal compounds show a high catalytic effect and accelerate the reaction remarkably as compared to the case wherein any of these metal compounds is not used. Every one of these metal compounds is soluble in water and since such a metal compound can be nearly completely removed together with the impurities and by-products in LC only by collecting CVL, which are separated out after finishing the reaction, by filtration and washing the thus collected CVL, the production of CVL of a high quality is carried out extremely satisfactorily.

In the process for continuously producing CVL from DABA and MH without separating the thus formed LC is particularly necessary to add MH into the aqueous mineral acid solution, which contains DABA. In the case where MH is thus slowly added, MH dissolves in the aqueous mineral acid solution and at the same time, MH reacts with DABA dissolved in the solution to form LC. Almost all of the thus formed LC separates from the solution except for a small amount thereof.

On the other hand, with the formation and separation of LC, DABA which has been in a non-dissolved state begins to dissolve and finally, all of DABA reacts with MH.

After the addition of MH is finished, and the reaction of DABA and MH is completely finished, the reaction mixture is subjected to filtration, and the thus obtained residue is washed with water to the neutrality and dried it, thereby obtaining the dried crude product. As the result, the dried product containing an amount of LC corresponding to 90% of the theoretical amount is obtained. However, in the present invention, a reaction mixture containing LC is used as the starting material of the next step (oxidation reaction).

Namely, the pH of the reaction mixture containing LC obtained in the first step is changed into from 2.0 to 4.0, and in the reaction mixture showing the pH in the above-mentioned range, LC of from 80 to 90% separates, and the rest of LC exists stably in a dissolved state.

In the case when air, oxygen or a gas containing oxygen is blown into the reaction mixture containing LC and oxidation of LC is carried out, a part of LC which is present in the reaction mixture containing LC in a dissolved state is oxidized into CVL and the thus formed CVL separates, and at the same time, LC which has been in the non-dissolved state in the solution dissolves in the solution. The reaction proceeds in the same way as mentioned above. Thus, a reaction mixture containing CVL in an amount of more than 90% of the theoretical amount is finally obtained. However, in the oxidation of LC, the yield of CVL depends largely on the presence or absence of the catalyst comprising the compound of a transition metal and, for instance, the yield of 90% attained in the presence of the transition metal compound(s) is changed into some dozen percentage in the case when the catalyst is not added.

In the continuous process without separating LC, it is preferable that DABA in the aqueous mineral acid solution and MH slowly added to the aqueous solution are made to be particles as minute as possible in order to advance the reaction of DABA and MH and to form and separate LC in a state as minute as possible. The mean particle diameter of DABA is preferably not larger than 30 μm, preferably not larger than 5 μm, and on the other hand, that of MH is preferably not larger than 50 μm, preferably not larger than 10 μm.

MH processed into a powdery form of the particle size may be slowly added into the aqueous mineral acid solution containing DABA or after preparing an aqueous dispersion containing the powdery form of MH, the thus prepared aqueous dispersion may be slowly added into the aqueous mineral acid solution containing DABA. The latter method of adding the aqueous dispersion of MH is particularly preferably in the view point that the dissolution of MH into the aqueous mineral acid solution containing DABA can be carried out with a favorable reproducibility without regard to the purity of MH.

According to the process of the present invention for producing CVL by oxidation of LC, it is possible to obtain CVL of an extremely high quality in a high yield and in a short period and accordingly, the process of the present invention is an excellent process also economically.

Furthermore, according to the process of the present invention, LC of a high quality can be obtained in a high yield by reacting DABA with MH in an aqueous mineral acid solution of pH of from 1.5 to 3.0.

Still more, according to the continuous process without separating LC according to the present invention, it is possible to effectively combine the LC-formation reaction from DABA and MH as the first step with the CVL-formation by oxidation of LC as the second step. Accordingly, it is possible to produce an amount of CVL of not less than 90% of the theoretical amount without carrying out the isolation and purification of LC.

Besides, in a final reaction mixture of the present invention, the unreacted DABA and MH, the impurities in the raw materials, i.e., DABA and MH, and the by-products of the reactions dissolve well, and only CVL separates substantially in an undissolved state. Accordingly, it is possible to easily obtain CVL of a high quality only through the steps of filtering the thus separated CVL and washing the thus collected CVL with water.

The present invention is explained in more detail in the following Examples; however, it should be recognized that the scope of the present invention is not restricted to these Examples.

EXAMPLE 1:

Into 500 ml of an aqueous 4.9% by weight solution of sulfuric acid, 177 g of DABA (containing 173 g of pure DABA in particles of a mean particle diameter of not larger than 30 μm) were added and after further adding 1 g of SCOUROL ® #100 (made by KAO-ATLAS CO.) to the thus formed mixture, a mixture of 284 g of MH (containing 270 g of pure MH in particles of a mean particle diameter of not larger than 50 μm) and 500 ml of water was added to the mixture within 10 hours at 70° C. under agitation. After the reaction was over, the reaction mixture was subjected to filtration and the residue was washed with water to the neutral point to obtain 391 g of the dried crude product (containing an amount of LC corresponding to 92% of the theoretical amount).

EXAMPLE 2

In quite the same manner as in Example 1 except for using 310 g of MH (containing 270 g of pure MH in particles of a mean particle diameter of not larger than 10 μm) instead of 284 g of MH (containing 270 g of pure MH in particles of a mean particle diameter of not larger than 50 μm) in Example 1, 387 g of the dried crude product (containing an amount of LC corresponding to 90% of the theoretical amount) were obtained.

EXAMPLE 3

In quite the same manner as in Example 1 except for adding MH within 5 hours, 390 g of the dried crude product (containing an amount of LC corresponding to 90% of the theoretical amount) were obtained.

EXAMPLE 4

In quite the same manner as in Example 1 except for using an aqueous 9.8% by weight solution of sulfuric acid instead of the aqueous solution of sulfuric acid in Example 1, 387 g of the dried crude product (containing an amount of LC corresponding to 88% of the theoretical amount) were obtained.

EXAMPLE 5

Into 46.3 g of industrial LC (containing 41.7 g of pure LC in particles of a particle diameter of from 10 to 20 μm), 250 g of an aqueous 1% by weight solution of sulfuric acid, 0.05 g of copper sulfate and 0.1 g of SCOUROL® #100 (made by KAO-ATLAS Co.) were added, and air was introduced into the thus formed mixture at a rate of 100 ml/min for 10 hours at 90° C. under agitation. After the reaction was over, the reaction mixture was subjected to filtration and the residue was washed with water to the neutrality to obtain 41.1 g of the dried crude product (containing an amount of CVL corresponding to 97% of the theoretical amount) of a melting point of from 172° to 175° C.

COMPARATIVE EXAMPLE

In quite the same manner as in Example 5 except for not adding copper sulfate to LC, 37.5 g of the dried crude product (containing an amount of CVL corresponding to 12% of the theoretical amount) were obtained.

EXAMPLE 6

In quite the same manner as in Example 5 except for adding 0.1 g of cobalt chloride instead of copper sulfate in Example 5, 40.5 g of the dried crude product of a melting point of from 171° to 175° C. (containing an amount of CVL corresponding to 95.6% of the theoretical amount) were obtained.

EXAMPLE 7

In quite the same manner as in Example 5 except for introducing oxygen at ordinary pressure into the reactant solution for 5 hours until the solution was saturated, instead of air in Example 5, 40.8 g of the dried crude product of a melting point of from 172° to 175° C. (containing an amount of CVL corresponding to 97% of the theoretical amount) were obtained.

EXAMPLE 8

Into 500 ml of an aqueous 4.9% by weight solution of sulfuric acid, 177 g of DABA (containing 173 g of pure DABA in particles of a mean particle diameter not larger than 30 μm) were added and after adding 1 g of SCOUROL® #100 (made by KAO-ATLAS Co.) into the thus formed mixture, a mixture of 500 ml of water and 284 g of MH (containing 270 g of pure MH in particles of a mean particle diameter not larger than 50 μm) was added to the thus formed mixture at 70° C. within 10 hours under agitation.

After 2 hours of the addition, 1500 ml of water and 0.5 g of copper sulfate were added to the mixture, and air was introduced to the mixture at a rate of 100 ml/min for 10 hours at 90° C. under agitation. After the reaction was over, the reaction mixture was subjected to filtration and the residue was washed with water to the neutrality to obtain 410 g of the dried crude product of a melting point of from 172° to 175° C. (containing an amount of CVL corresponding to 94% of the theoretical amount).

EXAMPLE 9

In the same manner as in Example 8 except for adding 310 g of MH (containing 270 g of pure MH in particles of a mean particle diameter of not larger than 10 μm) instead of 284 g of MH (containing 270 g of pure MH in particles of a mean particle diameter not larger than 50 μm) in Example 8, 415 g of the dried crude product of a melting point of from 171° to 178° C. (containing an amount of CVL corresponding to 92% of the theoretical amount) were obtained.

EXAMPLE 10

In the same manner as in Example 8 except for adding the same amount of the same MH within 5 hours instead of 10 hours in Example 8, 412 g of the dried crude product of a melting point of from 172° to 175° C. (containing an amount of CVL corresponding to 93% of the theoretical amount) were obtained.

EXAMPLE 11

In the same manner as in Example 8 except for using 500 ml of an aqueous 9.8% by weight solution of sulfuric acid instead of the aqueous solution of sulfuric acid in Example 8, 395 g of the dried crude product of a melting point of from 170° to 178° C. (containing an amount of CVL corresponding to 90% of the theoretical amount) were obtained.

EXAMPLE 12

In the same manner as in Example 8 except for using 1 g of cobalt chloride instead of 0.5 g of copper sulfate in Example 8, 406 g of the dried crude product of a melting point of from 172° to 175° C. (containing an amount of CVL corresponding to 93% of the theoretical amount) were obtained.

EXAMPLE 13

In the same manner as in Example 8 except for introducing oxygen at ordinary pressure to the reaction solution for 5 hours until the solution was saturated by oxygen instead of introducing air in Example 8, 412 g of the dried crude product of a melting point of from 172° to 175° C. (containing an amount of CVL corresponding to 93% of the theoretical amount) were obtained.

What is claimed is:

1. A process for producing 3,3-bis (4-dimethylaminophenyl)-6-dimethylaminophthalide, which comprises oxidizing 2-(4,4' bis(dimethylamino)benzhydryl)-5-dimethylaminobenzoic acid in the form of minute particles of a mean particle diameter of not larger than 20 μm in an aqueous solution of sulfuric acid of a pH of from 2.0 to 4.0 with air or oxygen in the presence of at least one catalyst selected from the group consisting of the chlorides and sulfates of copper and cobalt at a temperature of from 40° to 120° C.

2. A process for producing 3,3-bis (4-dimethylaminophenyl)-6-dimethylaminophthalide, which comprises slowly adding tetramethyl-4-4'-dimethylaminobenzhydrol in the form of minute particles of a mean particle diameter of not larger than 50 μm to a suspension containing m-dimethylaminobenzoic acid in the form of minute particles of a mean particle diameter of not larger than 30 μm in an aqueous solution of sulfuric acid of a pH of from 1.5 to 3.0 at a temperature of from 50° to 100° C., adding at least one catalyst selected from the group consisting of the chlorides and sulfates of copper and cobalt to the reaction mixture, an oxidizing the thus formed 2-(4,4'-bis(dimethylamino)benzhydryl)-5-dimethylamino benzoic acid in the resultant reaction mixture with air or oxygen at a temperature of from 40° to 120° C.

3. A process for producing 2-(4,4'-bis-(dimethylamino)benzhydryl)-5-dime benzoic acid, which comprises adding tetramethyl-4,4'-dimethylaminobenzhydrol in the form of minute particles of a mean particle diameter of not larger than 50 μm to a suspension containing m-dimethylaminobenzoic acid in the form of minute particles of a mean particle diameter of not larger than 30 μm to an aqueous solution of sulfuric acid of a pH of from 1.5 to 3.0 at a temperature of 50° to 100° C.

* * * * *